US008361481B2

(12) United States Patent
Hara et al.

(10) Patent No.: US 8,361,481 B2
(45) Date of Patent: Jan. 29, 2013

(54) LACTIC ACID BACTERIUM HAVING ANTI-ALLERGIC ACTIVITY AND PHARMACEUTICAL COMPOSITION

(75) Inventors: Takashi Hara, Niigata (JP); Toshio Joh, Niigata (JP); Takehisa Kumagai, Niigata (JP); Mariko Saito, Niigata (JP); Kimiko Uchiyama, Niigata (JP)

(73) Assignee: Kameda Seika Co., Ltd., Niigata (JP)

( * ) Notice: Subject to any disclaimer, the term of this patent is extended or adjusted under 35 U.S.C. 154(b) by 64 days.

(21) Appl. No.: 12/989,052

(22) PCT Filed: Apr. 24, 2009

(86) PCT No.: PCT/JP2009/058141
§ 371 (c)(1),
(2), (4) Date: Oct. 21, 2010

(87) PCT Pub. No.: WO2009/131208
PCT Pub. Date: Oct. 29, 2009

(65) Prior Publication Data
US 2011/0038891 A1 Feb. 17, 2011

(30) Foreign Application Priority Data

Apr. 25, 2008 (JP) ................. 2008-115091

(51) Int. Cl.
*A61K 39/02* (2006.01)
*C12N 1/20* (2006.01)
(52) U.S. Cl. .................. 424/234.1; 435/252.9
(58) Field of Classification Search .......... None
See application file for complete search history.

(56) References Cited

FOREIGN PATENT DOCUMENTS

| EP | 1634600 A1 | 3/2006 |
| JP | 2008-61513 A | 3/2008 |
| KR | 2003-0082950 A | 10/2003 |
| KR | 2007-0030961 A | 3/2007 |
| WO | 2004 096246 A1 | 11/2004 |

OTHER PUBLICATIONS

Database DDBJ/EMBL/GenBank[online], AccessionNo. CP000423 AAGR01000000 AAGR01000001-AAGR01000188, *Lactobacillus casei* ATCC334<http://www.ncbi.nlm.nih.gov/sviewer/viewer.fcgi?116103724:NCBI:193202026> uploaded on Nov. 10, 2007, retrieved on Jul. 14, 2009.
Database DDBJ/EMBL/GenBank [online] AccessionAAGR00000000 <http://www.ncbi.nlm.nih.qov/sviewer/viewer.fcgi?62465265:WGS:25353232>*Lactobacillus casei* ATCC334, uploaded on Oct. 17, 2006, retrieved on Jul. 14, 2009.
Database DDBJ/EMBL/GenBank [online] AccessionNo. D86517 *Lactobacillus casei* ATCC 334, 16Sribosomal RNA <http://www.ncbi.nlm.nih.gov/sviewer/viewer.fcgi?1843427:DDBJ:4398124>Uploaded on Jun. 6, 2002, Retrieved on Jul. 14, 2009.

Database DDBJ/EMBL/GenBank online AccessionNo. DQ199664 *Lactobacilus paracasei* <http://www.ncbi.nlm.nih.gov/sviewer/viewer.fcgi?76593947:NCBI11062971> Uploaded on Oct. 5, 2005, retrieved on Jul. 14, 2009.
Database DDBJ/EMBL/GenBank [online] AccessionNo. D79212 *Lactobacillus paracasei* subsp.Paracasei 16s ribosomal RNA <http://www.nlm.nih.gov/sviewer/viewer.fcgi?1808583:DDBJ:4398511> Uploaded on Jan. 28, 2003 retrieved on Jul. 14, 2009.
Database DDBJ/EMBL/GenBank [online] AccessionNo. AJ44105 *Lacatobacillus paracasei* 16Sribosomal RNA <http://www.ncbi.nlm.nih.gov/sviewer/viewer.fcgi?57282096:EMBL:10445458>Uploaded on Jan. 7, 2005, Retrieved on Jul. 14, 2009.
Database DDBJ/EMBL/GenBank [online] AccessionNo. AF385770 *Lactobacillus casei* BL23 <http://www.ncbi.nlm.nih.gov/sviewer/viewer.fcgi?14583099:NCBI:4549736>Uploaded on Mar. 14, 2003, Retrieved on Jul. 14, 2009.
Toshiyuki Watanabe and Takehisa Kumagai, 'Kome noKinosei Kaihatsu to Kodo Riyo -KomeTanpakushitsu to Shokubutsusei Nyusankin',Food chemicals, 2007, vol. 23, No. 4, pp. 24 to 28.
Fujiwara D., et al., "The anti-allergic effects of lactic acid bacteria are strain dependent and mediated by effects on both Th1/Th2 cytokine expression and balance" Int. Archives of Allergy and Immunology, 2004, vol. 135, No. 3, p. 205-215.
Takehisa Kumagai et al., 'Genmai Shinseki Jino Nyusankin Tenka Koka', Journal of the Japanese Society for Food Science and Technology, 2006, vol. 53, No. 3, pp. 179 to184.
Nobuo Sugano et al., 'Komenuka to Nyu o Genzairyo toshite Hakko Shokuhin no Kaihatsuni Kansuru Kenkyu', Reports of Kochi Prefectural Industrial Technology Center, 2001, No. 32, pp. 21 to 29.
Kumagai, T., et al., "Effect of *Lactobacillus casei* subsp.casei 327 on the growth of bifidobacteria and its survival in the intestine"Food Sci. Technol. Res., 2004, vol. 10, No. 2, p. 143-146.
Shuichi Uenogawa, 'Kafunsho nimo Koka!? Yoghurtde Menekiryoku Up', Shoku to Kenko, 2005, 2 Gatsugo, pp. 52 to 57.
International Search Report for PCT/JP2009/058141 dated Jul. 23, 2009.
European Search Report issued to European Patent Application No. 09735409.6 mailed Feb. 2, 2012.
"*Lactobacillus paracasei* strain DJ116s ribosomal RNA gene, partial sequence," XP002667591 retrieved from EBI accession No. EM_PRO:DQ462440 Database accession No. DQ462440 , 2006.
Notice of Reasons for Rejection issued to Kr Application No. 10-2010-7024121, mailed Mar. 16, 2012.

*Primary Examiner* — Padma Baskar
(74) *Attorney, Agent, or Firm* — Hoffmann & Baron, LLP

(57) ABSTRACT

An object aims to develop a lactic acid bacterium having an anti-allergic activity, which can be grown by using rice, particularly polished white rice, and can be collected, cooked and ingested together with rice in such a state that the lactic acid bacterium is attached to the surface of the rice. Another object aims to develop a food composition and a pharmaceutical composition, each of which comprises rice containing the lactic acid bacterium as a material. Thus, disclosed are: a lactic acid bacterium *Lactobacillus paracasei* K71 strain which has been internationally deposited in National Institute of Advanced Industrial Science and Technology, International Patent Organism Depositary under Accession No. FERM BP-11098; an anti-allergic agent comprising the lactic acid bacterium; a food composition comprising the anti-allergic agent; a food composition comprising rice which has been fermented with the lactic acid bacterium, a crushed product of the rice, or a cooked product of the rice or the crushed product of the rice; and a pharmaceutical composition comprising the anti-allergic agent.

13 Claims, 4 Drawing Sheets

LACTIC ACID BACTERIUM HAVING ANTI-ALLERGIC ACTIVITY AND PHARMACEUTICAL COMPOSITION

CROSS-REFERENCE TO RELATED APPLICATIONS

This application is the National Stage of International Application No. PCT/JP2009/058141, which designates the U.S., filed Apr. 24, 2009 which claims the benefit of JP 2008-115091, filed Apr. 25, 2008, the contents of which are incorporated by reference herein.

TECHNICAL FIELD

The present invention relates to a novel lactic acid bacterium, an anti-allergic agent including the lactic acid bacterium, and a food and pharmaceutical composition including the anti-allergic agent. More specifically, the present invention relates to a lactic acid bacterium *Lactobacillus paracasei* K71 strain which has been internationally deposited in the National Institute of Advanced Industrial Science and Technology, International Patent Organism Depositary under Accession No. FERM BP-11098, an anti-allergic agent comprising the lactic acid bacterium, and a food composition and a pharmaceutical composition comprising the anti-allergic agent.

BACKGROUND ART

The number of patients suffering from allergies is steadily increasing. For example, survey results in Japan have reported that one in three people suffer from some type of allergic disease. A reduction in the number of patients suffering from an allergic disease resulting from use of a food would have a high social and economic significance due to the resulting improvement in the national quality of life and the large decrease in medical costs.

IgE is a principal factor in immediate allergy (type-I allergy) reactions such as atopic dermatitis, hay fever or the like. IgE production is induced by B cells undergoing IgE class switching in response to interleukin 4 (IL-4). The principal source of production of IL-4 is $T_H2$ cells. Helper T cells such as $T_H1$ cells and $T_H2$ cells are stimulated by presentation of antigen from cells such as dendritic cells, macrophages or the like, and follow respective differentiation paths in response to the influence of cytokines such as IL-4, IL-12, or the like. The differentiation of $T_H1$ cells is induced by IL-12 and the differentiation of $T_H2$ cells is induced by IL-4. When $T_H2$ cells become particularly dominant due to collapse of the balance between $T_H1$ cells and $T_H2$ cells due to some reason, the effect of IL-4 is increased and IgE production is enhanced. The produced IgE binds with high-affinity IgE receptors on the cell surface of mast cells or basophils. In this state, when an antigen (allergen or the like) binds with IgE, cross-linking occurs between high-affinity IgE receptors and degranulation results in release of chemical messengers such as histamine or the like. Consequently lipid mediators such as leukotoriene are produced thereby resulting in allergic symptoms typified by inflammation. Serious allergic symptoms are observed during enhanced production of IgE.

Therapeutic agents for allergic diseases are mainly steroidal agents used as anti-inflammatory agents, or antagonists of chemical messengers, typically anti-histamine agents. All these agents are used in symptomatic treatment, and have no function of directly reducing the amount of IgE which is the main factor in pathogenesis. Furthermore the former agents entail risks associated with side effects such as drowsiness or dryness of the mouth, and the latter agents have side effects such as suppression of the overall immunity system. Medicines that can mitigate a state in which $T_H2$ cells are particularly dominant aim to enable definitive therapy for allergies, however at present such agents have not yet been developed. Hyposensitization therapy is a therapeutic method of reducing an amount of IgE. A method of hyposensitization therapy is a therapeutic method which mitigates symptoms by ingesting (or injecting) an allergen which is the causal substance of an allergic illness commencing with a small amount and gradually increasing the amount. This therapeutic method includes a risk of anaphylaxis due to administration of the allergen, and must be performed under strict medical supervision. At the present time, hyposensitization therapy cannot be said to have been completed validated, and scope for improvement in relation to reliability remains in view of the long time required for treatment and the individual differences that are observed.

Against this background, lactic acid bacteria have attracted attention due to the rich experience in their ingestion as a food and due to their function of suppressing IgE production. The anti-allergic action of lactic acid bacteria is strain-specific. Lactic acid bacteria having this type of anti-allergic action are screened and enter the market in the form of lactic acid drinks or yoghurt.

Although continuous daily ingestion of lactic acid bacteria is necessary to profit an anti-allergic action, individual tastes may preclude consumption of yoghurt or lactic acid bacteria drinks. Furthermore it is unlikely that these foods are in an optimal configuration for daily required ingestion without a Japanese person becoming satiated. In contrast, the staple of the Japanese diet is rice, and although a tendency not to eat rice has been evident in recent years, rice is a product that will always be ingested at least in one out of three meals.

A lactic acid bacterium having an anti-allergic action can be combined with rice by mixing polished white rice with a lactic acid bacterium that has been cultivated in a separate tank or the like. However since the diameter and the specific gravity of the rice particles and those of the lactic acid bacteria are different, there is a risk that these components will separate during storage, and that only the lactic acid bacteria will sink to the bottom of a storage vessel such as a rice bag or the like. Consequently, it will not always be the case that a desired amount of lactic acid bacteria will be contained in rice even when a fixed amount of rice is measured. Consequently, there are difficulties associated with ensuring ingestion of a required amount of lactic acid bacteria in order to display an anti-allergic action. Furthermore although a technique of coating lactic acid bacteria onto the surface of the polished white rice can be used, such a technique requires complicated processing and causes cost increases.

DISCLOSURE OF THE INVENTION

Problems to be Solved by the Invention

Therefore there is a need for the development of a lactic acid bacterium having an anti-allergic action that can be grown using rice, and in particular polished white rice, that can be recovered as attached to the rice surface together with the rice, and that can be cooked and ingested, in addition to a food composition and a pharmaceutical composition using rice containing a lactic acid bacterium as an ingredient.

Means for Solving the Problems

The present invention provides a lactic acid bacterium *Lactobacillus paracasei* (hereinafter the genus *Lactobacillus* will be abbreviated to "L.") K71 strain which has been internationally deposited in the National Institute of Advanced Industrial Science and Technology, International Patent Organism Depositary (AIST Tsukuba Central 6, 1-1, Higashi 1-chome Tsukuba-shi, Ibaraki-ken 305-8566 Japan), pursuant to the Budapest Treaty on Feb. 20, 2009 under Accession No. FERM BP-11098.

The present invention provides an anti-allergic agent comprising the lactic acid bacterium according to the present invention.

The lactic acid bacteria in the anti-allergic agent according to the present invention may be a live bacterium.

The lactic acid bacteria in the anti-allergic agent according to the present invention may be a killed bacterium.

The anti-allergic agent according to the present invention may include a bacterial component of the lactic acid bacterium according to the present invention.

The present invention provides a food composition including the anti-allergic agent according to the present invention.

The present invention provides a pharmaceutical composition including the anti-allergic agent according to the present invention.

The present invention provides a food composition including fermented rice using the lactic acid bacterium according to the present invention, a pulverized product of the rice, or cooked rice obtained by cooking the above rice or the pulverized rice product.

The present invention provides a method of manufacturing an anti-allergic agent including the steps of inoculating a medium with the lactic acid bacterium according to the present invention, and cultivating.

The medium used in the method of manufacturing the anti-allergic agent according to the present invention may be rice or a pulverized rice product.

In the present invention, the anti-allergic agent may be a medicine containing a component being a substance having an action of suppressing or inhibiting an allergic reaction. The point of action of an anti-allergic agent includes, but is not limited to, the differentiation process of $T_H2$ cells, the process of antigen presentation to the $T_H2$ cells, the process of proliferation and activation of the $T_H2$ cells, the process in which B cells undergo IgE class switching by interaction with the $T_H2$ cells and mature into IgE-producing cells, the process of differentiation, proliferation and activation of all helper T subsets ($T_H1$, $T_H2$, $T_H3$ (suppressor T cells), $T_H17$, $T_{reg}$ (regulatory T cells) and the like), and cytotoxic T cells, NKT cells, and natural killer cells, the process of immunological regulation including IgE production mediated by the action of helper T subsets ($T_H1$, $T_H2$, $T_H3$ (suppressor T cells), $T_H17$, $T_{reg}$ (regulatory T cells) and the like), and cytotoxic T cells, NKT cells, and natural killer cells, the process of enhancement of IgE production due to the presence of an allergen, the process of differentiation, proliferation and activation effector cells such as mast cells, basophils, eosinophils, and the like, the process of synthesis of chemical messengers such as histamine in the effector cells, accumulation as granules together with the process of new synthesis of mediators such as leukotoriene, the process of formation of a composite binding a high-affinity IgE receptor on the effector cell to IgE and an allergen, the process of degranulation resulting from signaling caused by formation of such a composite, and the process of chemical messengers such as histamines or leukotoriene released as a result of degranulation inducing localized anaphylaxis in the skin, respiratory organs, digestive organs, eyes, nose, and various other organs.

The anti-allergic agent according to the present invention has an action that suppresses or inhibits at least one of the above processes. The points of action of the anti-allergic agent are such that although the differentiation and maturation process of $T_H2$ cells are promoted by IL-4, IL-12 suppresses the differentiation and maturation process of $T_H2$ cells by promoting the differentiation and maturation process of $T_H1$ cells. Thus the differentiation and maturation process of $T_H2$ cells can be suppressed by suppressing IL-4 production and promoting IL-12 production. The anti-allergic agent according to the above mechanism is a therapeutic agent that can be used etiotropically in relation to allergic diseases. Furthermore such an agent is preferred due to the absence of side-effect risks such as those associated with anti-histamines or steroidal agents.

The lactic acid bacterium according to the present invention has an anti-allergic action, and has been screened by the testing described in the following embodiments, as a lactic acid bacterium enabling superior growth on the surface of polished white rice. Any condition can be used as long as the condition enables growth of the bacterium, and the liquid culture for the lactic acid bacterium according to the present invention can be cultivated under normal cultivation conditions using a normal medium used for cultivation of a lactic acid bacterium (for example, MRS broth, or vegetable/fruit juices). The pH of the medium when culturing is commenced is between 4.0 and 7.0, and preferably between 6.0 and 6.5. The culture temperature is between 35° C. to 42° C. and preferably from 37° C. to 40° C. Although sufficient growth is possible using static culturing, gentle shaking is preferred to uniformly disperse the bacteria and the culturing components. As lactic acid accumulates in the medium as a result of growth of lactic acid bacteria, the pH of the medium gradually falls. Although lactic acid bacteria can be collected to a certain degree without control of the pH in the medium, control of the pH of the medium is preferably performed by addition of calcium carbonate to the medium or automatic pH control. A high density of lactic acid bacteria can be obtained by controlling the pH of the medium to 4.0 to 7.0, and preferably to 6.0 to 6.5.

As shown by the following embodiments, an anti-allergic action is demonstrated in microbial cells produced by heating and killing the lactic acid bacterium according to the present invention. Therefore lactic acid bacterium contained in the anti-allergic agent according to the present invention may include living cells, more specifically, microbes undergoing propagation and/or metabolic processes, or killed cells, more specifically, microbes which are not undergoing propagation or metabolic processes. The anti-allergic agent according to the present invention may be a microbial cell component of the lactic acid bacterium according to the present invention, or may include a component having an anti-allergic action.

The food composition according to the present invention may include a component such as a seasoning, colorant, preservative, or other component permitted as a food product in addition to the anti-allergic agent according to the present invention. The food composition according to the present invention may be manufactured by fermentation using the lactic acid bacterium according to the present invention as long as maintaining the effect of the anti-allergic agent according to the present invention. Manufacturing may be performed by cooking, or otherwise heating, pressurizing or the like, the lactic acid bacterium according to the present invention and/or a fermented product produced using the lactic acid bacterium according to the present invention. The lactic acid bacterium according to the present invention grown by liquid culturing may be used without modification, or may be dried and used as a food product ingredient having an anti-allergic action, or in addition may be used as a starter when fermenting polished white rice.

When fermenting polished white rice using the lactic acid bacterium according to the present invention, the polished white rice is washed and then immersed in water, and fermented by addition of a starter including the lactic acid bacterium according to the present invention. The lactic acid bacterium according to the present invention undergoes vigorous growth through use of the nutrients on the surface of the rice, and adheres to the surface of the rice. Consequently even when fermentation is completed and the rice is placed into a sieve or the like, and thereafter is washed in water, almost all of the lactic acid bacteria remain attached to the rice surface. $10^8$ to $10^9$ lactic acid bacteria per 1 g of raw material rice are attached to the surface of polished white rice after completion of fermentation conducted under appropriate conditions. This rice can be dried and processed as raw material rice, or cooked rice containing the anti-allergic lactic acid bacteria can be obtained by direct addition to water and cooking without drying.

The pharmaceutical composition according to the present invention may contain a substance that is pharmaceutically required and/or a substance permitted for use as a pharmaceutical composition in addition to the anti-allergic agent according to the present invention.

According to the present invention, polished white rice having a uniform distribution of anti-allergic lactic acid bacteria on a surface thereof can be easily and cost-effectively obtained by the fermentation with the lactic acid bacterium according to the present invention that has an anti-allergic action with polished white rice as a raw material. Therefore a staple food can be provided that has an anti-allergic action and that can be cooked and ingested continuously on a daily basis.

PREFERRED MODE FOR CARRYING OUT THE INVENTION

Figure 1:
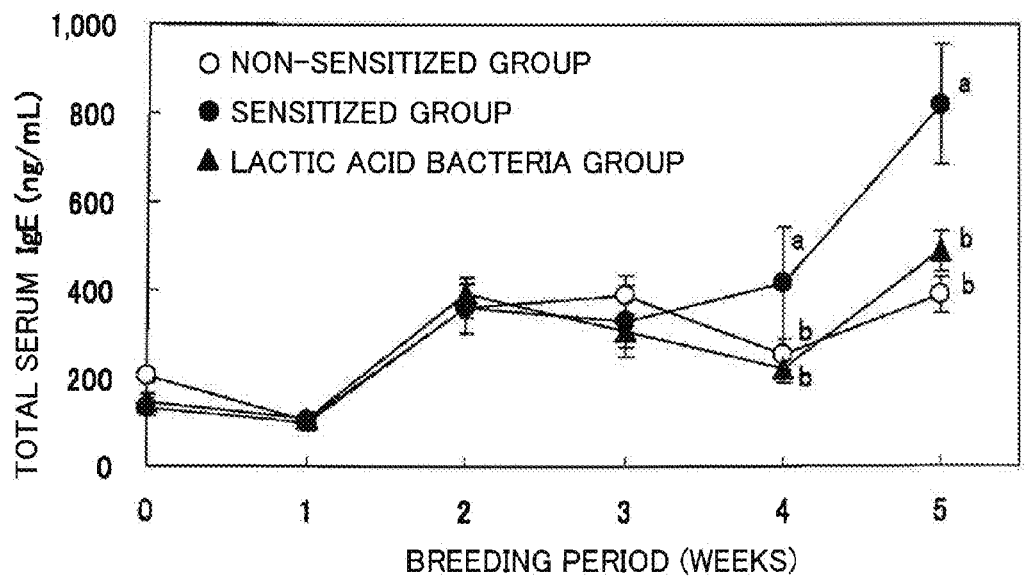
FIG. 1 is a graph showing the effect of repetitive oral administration of lactic acid bacteria on total serum IgE of ovalbumin (OVA) sensitized mice.

The present invention will be described in detail hereafter with respect to the embodiments of the present invention. However the present invention is not limited in any manner by these embodiments.

Example 1

1. Screening of lactic acid bacteria having an anti-allergic action and demonstrating superior growth on the surface of polished white rice.

(1) Source of Lactic Acid Bacteria Used in Screening

The lactic acid bacteria used in screening have been newly separately from fermented food products using rice as a raw material (including powdered rice husk, malted-rice bean paste, sake lees, and fermenting mash). The names of 39 lactic acid bacterial strains that were confirmed to belong to the genus *Lactobacillus* preliminary study are shown in Table 1.

(2) In Vitro Evaluation of Anti-Allergic Action of Lactic Acid Bacteria

Spleen cells extracted from an ovalbumin (OVA) sensitized mice were used to conduct anti-allergic testing in vitro. Three female mice purchased at six-weeks of age (Balb/c, Charles River) were housed under SPF conditions and subjected to a 0.5 mL intraperitoneal injection of a suspension of 1 mg/mL $Al(OH)_3$ and 2 mg/mL OVA per mouse at a frequency of once weekly. Thereafter blood was drawn appropriately from the caudal vein to confirm total serum IgE and the OVA specific IgE level. The measurement of total serum IgE and OVA specific IgE was performed by a sandwich ELISA method using a Murine Opt EIA ELISA set manufactured by Becton Dickinson Co., Ltd. More specifically, when total serum IgE is measured, suitably diluted blood serum is added to a plate coated with rat monoclonal anti-mouse IgE as a primary antibody, and then biotinized rat monoclonal anti-mouse IgE heavy chain antibodies are used as the secondary antibody. When measuring OVA specific IgE, an ELISA was performed in the same manner by using a plate coated with OVA as a substitute primary antibody. The individuals that have the highest level of both total serum IgE and OVA specific IgE are selected, and the spleen was excised 28 days after commencement of breeding. The excised spleen is finely dissected using a scalpel, a red blood cell lysis buffer (154 mM of ammonium chloride, 14 mM of sodium bicarbonate, and 0.11 mM of EDTA-2Na, pH 7.3) was added, and the red blood cells were removed. After diluting to $2 \times 10^6$ cells m/L in RPM 1640 medium containing 10% fetal calf serum (Difco), penicillin G (100 U/mL), streptomycin (100 mg/mL) and 10 mM HEPES, 100 µL titers were dispensed into a 96-well microtiter plate. Then, a 20 µL of a suspension of heat-killed lactic acid bacteria (1 mg/mL) and 80 µL of an OVA solution (1 mg/mL) were added. After culturing for 7 days in a 5% carbon dioxide atmosphere and a temperature of 37° C., the spleen cells and the lactic acid bacteria were removed by centrifugation of the culturing liquid. The respective concentrations of IL-4 and IL-12 in the supernatant were measured using Mouse IL-4 (Catalog No. 555232) and Mouse IL-12 (p 70, Catalog No. 555256) of a Mouse Opt EIA ELISA set manufactured by Becton Dickinson Co., Ltd.

(3) Growth Testing of Lactic Acid Bacteria with Respect to Polished White Rice Surface 50 g of the polished white rice is washed, and immersed in 100 mL of distilled water.

One mL of an overnight culture liquid of a lactic acid bacteria (approximately $10^9$/mL) at 37° C. in MRS broth is added to the immersion liquid and the mixture is maintained at a temperature of 38° C. for one day. The water is discarded, and after washing three times using approximately 100 mL of distilled water, the fermented rice is pulverized, and the lactic acid bacteria attached to the rice surface is released and suspended. The pulverization of the fermented rice was performed by placing 10 g of the fermented rice together with 90 mL of sterile physiological saline (0.85% NaCl) in a sterile bag provided with a designated filter, attaching to a stomacher (Organo, Stomacher 400-T), and pulverizing by operation at 230 rpm for 120 seconds. The pulverized fermented rice is suitably diluted, spread onto a LBS agar medium (BBL) and cultured to thereby calculate the amount of lactic acid bacteria attached to the surface of polished white rice according to the resulting number of colonies.

(4) Results

Anti-allergic activity and the results of the growth and attachment tests using polished white rice are shown in Table 1.

TABLE 1

| Name of Bacterial Strain | Cytokine Concentration (pg/ml) | | Growth of Polished White Rice ($\times 10^8$ cfu/g) |
| --- | --- | --- | --- |
| | IL-4 | IL-12 | |
| L. casei subsp casei K327 | 242 ± 50 | 148 ± 92 | |
| L. casei subsp casei K379 | 159 ± 39 | 334 ± 88 | |
| L. casei subsp casei K409 | 104 ± 7 | 172 ± 51 | |
| L. casei subsp casei K508 | 250 ± 14 | 179 ± 84 | |
| L. casei subsp casei K924 | 152 ± 62 | 241 ± 74 | |
| L. fermentum K1016 | 137 ± 35 | 275 ± 120 | |
| L. parabuchineri K17 | 203 ± 36 | 106 ± 65 | |
| L. paracasei K101 | 196 ± 20 | 256 ± 42 | |
| L. paracasei K102 | 175 ± 39 | 244 ± 84 | |
| L. paracasei K11 | 202 ± 28 | 321 ± 137 | |
| L. paracasei K110 | 151 ± 74 | 274 ± 89 | |
| L. paracasei K111 | 155 ± 1 | 92 ± 7 | |
| L. paracasei K112 | 88 ± 40 | 358 ± 119 | 0.2 |
| L. paracasei K115 | 79 ± 17 | 351 ± 32 | 1.2 |
| L. paracasei K121 | 153 ± 44 | 203 ± 101 | |
| L. paracasei K122 | 58 ± 11 | 996 ± 109 | 0.6 |
| L. paracasei K142 | 86 ± 19 | 348 ± 26 | 0.9 |
| L. paracasei K21 | 169 ± 58 | 206 ± 55 | |
| L. paracasei K41 | 254 ± 35 | 125 ± 57 | |
| L. paracasei K61 | 204 ± 111 | 164 ± 27 | |
| L. paracasei K62 | 130 ± 26 | 216 ± 18 | |
| L. paracasei K70 | 165 ± 27 | 98 ± 27 | |
| L. paracasei K71 | 69 ± 17 | 1183 ± 188 | 6.2 |
| L. paracasei K72 | 164 ± 5 | 169 ± 51 | |
| L. paracasei K91 | 203 ± 33 | 222 ± 94 | |
| L. pentosus K258 | 87 ± 43 | 524 ± 192 | 0.2 |
| L. plantarum K124 | 100 ± 29 | 677 ± 212 | 0.4 |
| L. plantarum K139 | 83 ± 18 | 465 ± 87 | 0.3 |
| L. plantarum K158 | 79 ± 33 | 595 ± 79 | 0.01 |
| L. plantarum K198 | 88 ± 5 | 513 ± 212 | 0.2 |
| L. plantarum K199 | 123 ± 47 | 706 ± 353 | |
| L. plantarum K204 | 99 ± 31 | 547 ± 63 | 0.09 |
| L. plantarum K246 | 87 ± 5 | 501 ± 287 | 0.004 |
| L. plantarum K413 | 115 ± 11 | 512 ± 9 | |
| L. plantarum K721 | 74 ± 6 | 337 ± 191 | 0.08 |
| L. plantarum K79 | 92 ± 20 | 559 ± 134 | 0.02 |
| L. reuteri K141 | 256 ± 81 | 111 ± 4 | |
| L. reuteri K142 | 281 ± 63 | 94 ± 56 | |
| L. sake K244 | 57 ± 11 | 800 ± 161 | 0.4 |

As shown in Table 1, of the 39 strains of lactic acid bacteria isolated from fermented food products using rice as a raw material, 15 strains displayed a conspicuous decrease in IL-4 concentration and a conspicuous increase in IL-12 concentration. IL-4 promotes differentiation and maturation of $T_H 2$ cells. On the other hand, IL-12 suppresses differentiation and maturation of $T_H 2$ cells by promoting differentiation and maturation of $T_H 1$ cells. When $T_H 2$ cells become particularly dominant due to collapse of the balance between $T_H 1$ cells and $T_H 2$ cells, the high-concentration IL-4 environment enhances production of IgE and induces an allergic state. Therefore lactic acid bacteria that suppresses IL-4 production and promotes IL-12 production mitigates a state in which $T_H 2$ cells are dominant, that is to say, such bacteria have an anti-allergic action. The lactic acid bacterium Lactobacillus paracasei K71 strain of the 15 strains of lactic acid bacteria having a strong anti-allergic action displays superior growth in relation to polished white rice, and is easily recovered due to strong adhesion of the polished white rice surface. Thus the lactic acid bacterium Lactobacillus paracasei K71 strain was selected as the optimal strain for the object of the present invention. The lactic acid bacterium Lactobacillus paracasei K71 strain will hereinafter be referred to as the lactic acid bacterium according to the present invention. The lactic acid bacterium according to the present invention was isolated from sake lees and has been internationally deposited in the National Institute of Advanced Industrial Science and Technology, International Patent Organism Depositary under Accession No. FERM BP-11098.

Example 2

2. Characterization of Lactic Acid Bacterium According to the Present Invention

Analysis of 16S rRNA Sequence

The sequence of a polynucleotide fragment in the 16S ribosomal RNA (hereinafter referred to as "rRNA") genetic region of a microorganism amplified according to method known to a person ordinarily skilled in the art using a microbial DNA template of the lactic acid bacterium Lactobacillus paracasei K71 strain according to the present invention is shown in Sequence No. 1. There are more than 489,840 types of microbial 16S rRNA. After alignment, whole length sequences or partial sequences of such rRNA has been used to create a database and can be used through the Ribosomal Database Project II ((RDP II, http://rdp.cme.msu.edu/) (Release 9.59, current at Mar. 5, 2008)) (Maidak, B. L et. al. 2001, Nucleic Acids Res., 29, pp. 173-174). As a result of searching the above database using the sequence in Sequence No. 1, 100% homology was found with a nucleotide sequence of a 16S rRNS gene in the JCM8130 strain of L. paracasei subsp. paracasei that is a variety of L. paracasei, and 99.9% homology was found with the NBRC15906 strain of L. paracasei subsp. tolerans. Although homology searching demonstrates that the nucleotide sequence of Sequence No. 1 has a high homology with the nucleotide sequence in the 16S rRNA gene of the ATCC334 strain of L. casei, the article by Dellaglio, F. et. al. asserts that this is the same for each strain of L. paracasei (Int. J. Syst. Evol. Microbiol., 52:285-287 (2002). However since it is surmised that there is a strong possibility that the ATCC334 strain of L. casei also belongs to L. paracasei, the fact that the ATCC334 strain of L. casei was found in a homology search does not allow a conclusion that the lactic acid bacterium according to the present invention belongs to L. casei. When cluster analysis is performed in relation to nucleotide sequences for microbial 16S rRNA genes having high hits in homology searches in relation to strains other than the ATCC334 strain of L. casei, the nucleotide sequence in Sequence No. 1 belongs to a cluster forming two varieties of L. paracasei, and is the same sequence as the nucleotide sequence for 16S rRNA genes in L. paracasei subsp. paracasei. Therefore the lactic acid bacterium according to the present invention according to the analytical results of the nucleotide sequences of 16S rRNA genes demonstrates a strong possibility of belonging to L. paracasei at a species level.

Physiological and Biochemical Testing

The results of various physiological and biochemical tests carried out on the lactic acid bacterium *Lactobacillus paracasei* K71 strain according to the present invention are shown below in Tables 2, 3, and 4.

TABLE 2

Results of the First Stage Test

| Test item | *Lactobacillus paracasei* K71 |
|---|---|
| Cultivation temperature (° C.) | 30 |
| Cellular morphology | rod |
| | (0.8-0.9 × 1.5-2.5 m) |
| Gram staining | + |
| Spore formation | − |
| Motility | − |
| Colony morphology | medium: MRS agar |
| | cultivation time: 24 hr |
| | diameter: 1.0-2.0 mm |
| | color: milky-white |
| | shape: circular |
| | elevation: lenticular |
| | edge: entire |
| | surface: smooth |
| | transparent: opaque |
| | consistency: butyrous |
| Growth test at (° C.) 37 | + |
| 45 | + |
| Catalase | + |
| Oxidase | + |
| Acid/gas from glucose | +/− |
| (acid production/gas production) | |
| O/F fast (oxidation/fermentation) | +/+ |

+: positive,
−: negative

TABLE 3

Results of Fermentation Test (second stage)
*Lactobacillus-paracasei* K71 strain

| glycerol | − | salicin | + |
|---|---|---|---|
| erythritol | − | cellobiose | + |
| D-arabinose | − | maltose | + |
| L-arabinose | − | lactose | + |
| ribose | + | melibiose | − |
| D-xylose | − | saccharose | + |
| L-xylose | − | trehalose | + |
| adonitol | + | inulin | − |
| β-methyl-D-xyloside | − | melicitose | + |
| galactose | + | raffinose | − |
| glucose | + | starch | − |
| fructose | + | glycogen | − |
| mannose | + | xylitd | − |
| sorbose | − | gentiobiose | − |
| rhamnose | − | D-turanose | + |
| dulcitol | − | D-lyxose | − |
| inositol | − | D-tagatose | + |
| mannitol | + | D-fucose | − |
| sorbitol | − | L-fucose | − |
| α-methyl-D-mannoside | − | D-arabitol | − |
| α-methyl-D-glucoside | + | L-arabitol | − |
| N-acetyl glucosamine | + | gluconate | + |
| amygdalin | + | ketogluconate | − |
| arbutin | + | 5-ketogluconate | − |
| esculin | + | | |

TABLE 4

Growth Tests:

| 10° C. | + |
|---|---|
| 40° C. | + |
| 45° C. | + |

The results of the bacterial first stage testing shown in Table 2 show that the lactic acid bacterium according to the present invention is a non-motile gram positive rod that ferments glucose, and is both catalase and oxidase negative. These characteristics correspond with the general characteristics of a lactic acid *bacillus* such as *L. paracasei* as suggested by the 16S rRNA gene nucleotide sequence analysis. The results of the bacterial second stage tests shown in Table 3 show that the lactic acid bacterium according to the present invention ferments ribose, adonitol, galactose, fructose, dulcitol, and the like, and does not ferment glycerol, D-arabinose, rhamnose, inositol, and the like. The results of the growth test shown in Table 4 show that the lactic acid bacterium according to the present invention was grown at 10° C. These characteristics are thought to coincide with the typical characteristics of *L. paracasei* (Collins, M. D. et. al., Int. J. Syst. Bacteriol., 39: 105-108 (1989) as suggested by the 16S rRNA gene nucleotide sequence analysis. Therefore the results of the various physiological and biochemical tests demonstrate a strong possibility that the lactic acid bacterium according to the present invention belongs to the *L. paracasei* subsp. *paracasei* at the subspecies level.

Example 3

In vivo Evaluation of Anti-Allergic Action of Lactic Acid Bacterium according to the Present Invention (1) Effect on Allergen Sensitized Mice IgE resulting from repetitive oral administration to allergen sensitized mice of *Lactobacillus paracasei* K71 strain that is the lactic acid bacterium according to the present invention, and the production of cytokines (IL-4) affecting allergies were examined using the method described below.

Eighteen female mice (Balb/c) at six weeks of age were purchased from Charles River Inc. and housed in a conventional environment. After 4 days of acclimatization, the mice were divided into three groups of six mice, and 50 μL of a microbial suspension (20 mg/mL) of *Lactobacillus paracasei* K71 strain that is the lactic acid bacterium according to the present invention was repetitively given by daily oral administration to one of the groups. One week after commencing administration, blood was drawn at a frequency of once a week from the caudal vein, and thereafter Al(OH)$_3$ and OVA were injected intraperitoneally using the same method as EXAMPLE 1. On the 42$^{nd}$ day after commencing testing, the spleen was removed after completion of blood collection using the same method as EXAMPLE 1, and splenic cells were sampled. The same blood collection and spleen extraction were performed in relation to a sensitized group which received daily oral administration of distilled water in substitution for a lactic acid bacterial suspension together with weekly intraperitoneal injections of a suspension of Al(OH)$_3$ and OVA, and a non-sensitized group which received oral administration of distilled water, and which did not receive intraperitoneal injections of a suspension of Al(OH)$_3$ and OVA.

Figure 2:
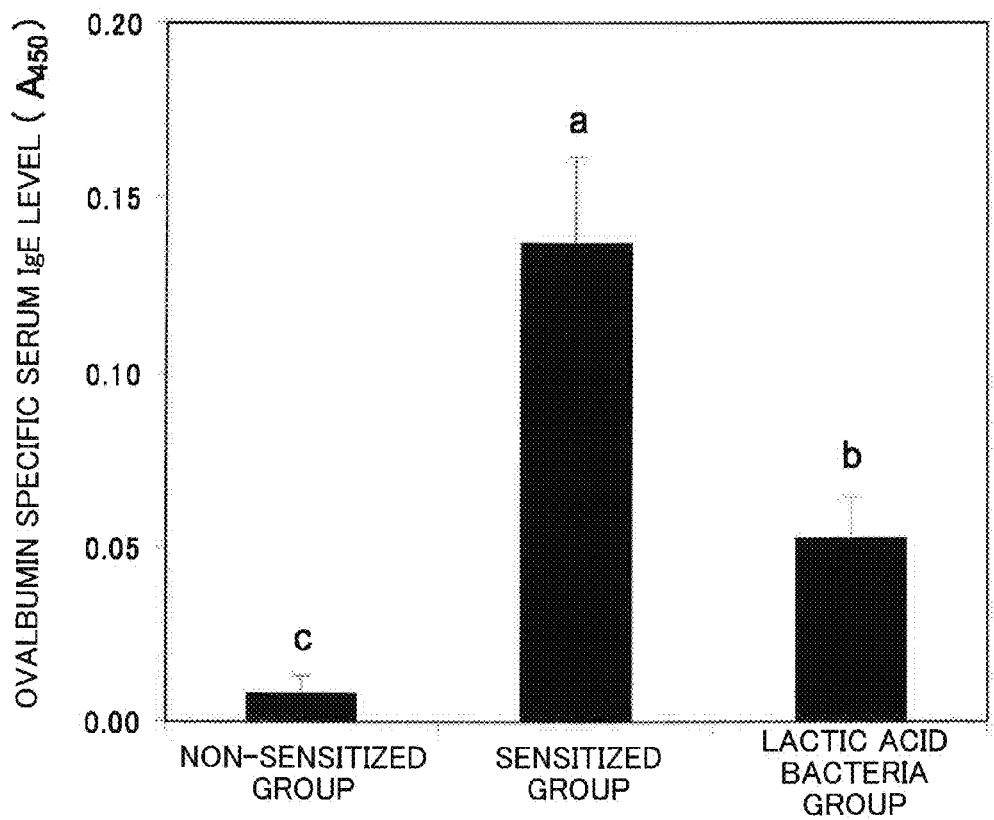
FIG. 2 is a graph showing the effect of repetitive oral administration of lactic acid bacteria on ovalbumin specific IgE levels in OVA sensitized mice.
Figure 3:
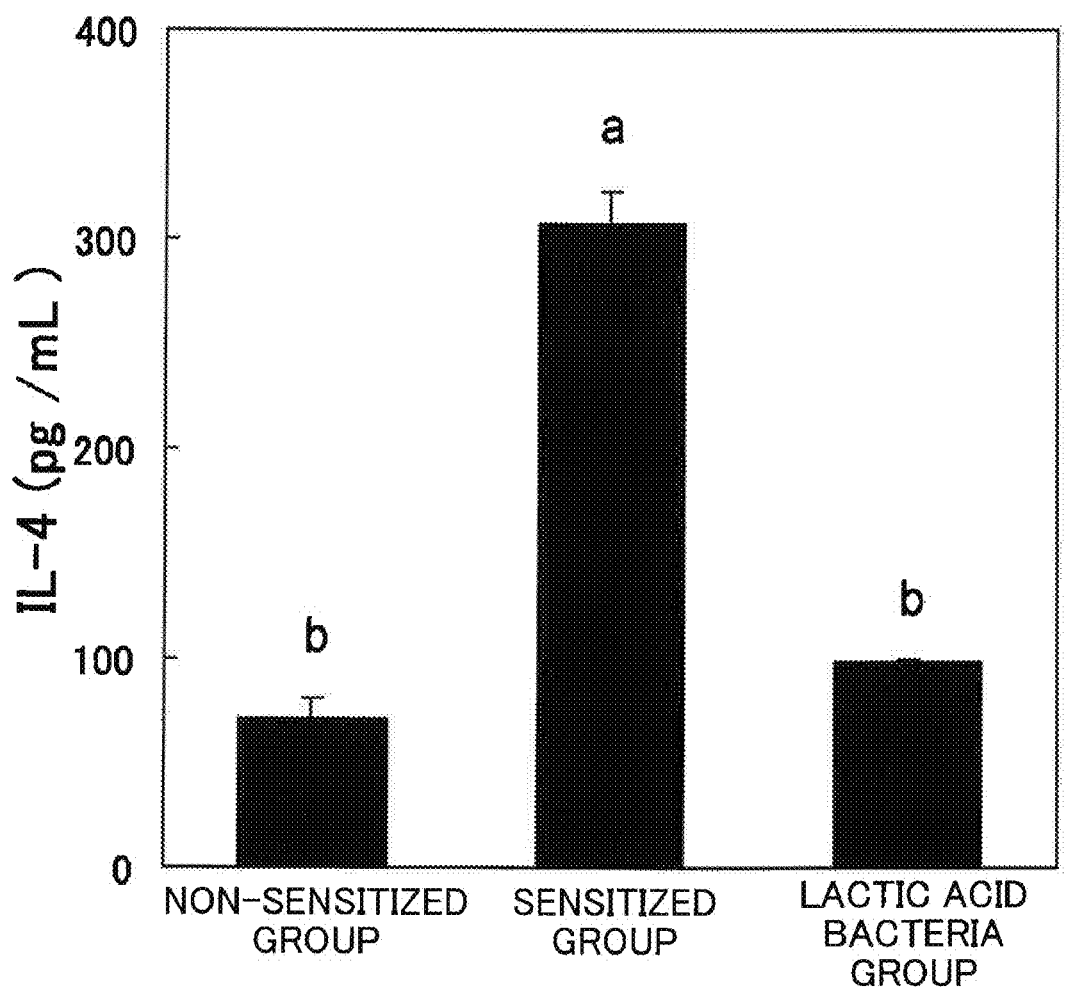
FIG. 3 is a graph showing the effect of repetitive oral administration of lactic acid bacteria on IL-4 production in splenic cells of OVA sensitized mice.
Figure 4:
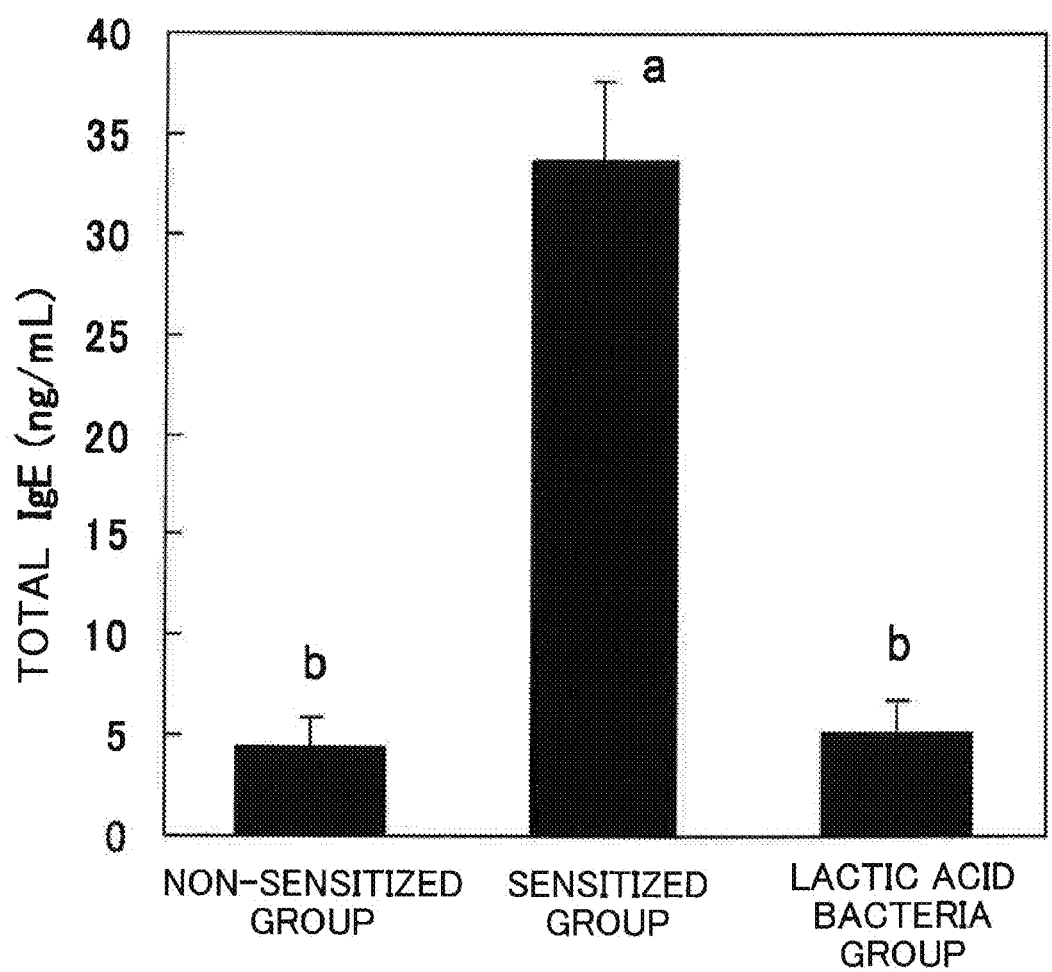
FIG. 4 is a graph showing the effect of repetitive oral administration of lactic acid bacteria on IgE production in splenic cells of OVA sensitized mice.

The collected plasma samples were analyzed for total serum IgE and OVA specific IgE levels using the same method as described in EXAMPLE 1. After adding 100 μg/mL of OVA, the splenic cells were cultured. The amount of IL-4 and IL-12 in the supernatant after 7 days was analyzed, and the total IgE was analyzed after 14 days. The effect of repetitive oral administration of the lactic acid bacteria on total serum IgE in OVA sensitized mice is shown in FIG. 1 and the effect on ovalbumin specific IgE levels is shown in FIG. 2. The effect of repetitive oral administration of the lactic acid bacterium on IL-4 production in the supernatant of OVA sensitized mice splenic cells is shown in FIG. 3 and the effect of repetitive oral administration of the lactic acid bacterium on total IgE in the supernatant of OVA sensitized mice splenic cells is shown in FIG. 4. In FIGS. 1 to 4, the notations (a) and (b) denote that the difference between the groups under the two test conditions is statistically significant (P<0.05), and the notation (c) denotes a statistically significant difference (P<0.05) for the group under experimental conditions (c) from either group under experimental conditions (a) or (b). As shown in FIG. 1 to FIG. 4, there is a significant increase in total serum IgE (FIG. 1) and ovalbumin specific IgE (FIG. 2) resulting from allergen sensitization. However the increases are significantly suppressed by repetitive administration of lactic acid bacteria. In a similar manner, repetitive oral administration of lactic acid bacteria causes a significant reduction in IL-4 production (FIG. 3), and total IgE production (FIG. 4) in splenic cells. The statistically significant difference between the groups subject to each experimental condition was verified using Fisher's PLSD for significant differences in one-way analysis of variance using Statcel which is add-in software for EXCEL, the spreadsheet software of Microsoft Corporation.

Example 4

Effect on Atopic Dermatitis Model Animal

The effect on the progression of atopic dermatitis of repetitive oral administration of lactic acid bacterium *Lactobacillus paracasei* K71 strain according to the present invention was examined using a NC mouse which is a model animal for atopic dermatitis.
Twelve female mice (Balb/c) at five weeks of age were purchased from Charles River Inc. and underwent three days' of acclimatization using CE-2 feed (CLEA Japan Inc.), and then were separated into two groups of six mice. One group was given CE-2 feed containing 0.05% dried bacteria of *Lactobacillus paracasei* K71 strain (lactic acid bacteria administration group) and the other group was given normal CE-2 feed (control group). Feeding continued for three weeks.

Allergy sensitization was performed using picryl chloride (2,4,6-trinitrochlorobenzene, used after re-crystalization). Initial sensitization was performed by coating a 5% picryl chloride solution (dissolved in ethanol:acetone=4:1) on the abdomen and the pads of four limbs. After four days, coating on the ear was repeated at a frequency of once weekly for a total of 8 administrations using 1% picryl chloride solution (dissolved in edible olive oil). Blood collection and analysis of total serum IgE was performed appropriately using the method described in EXAMPLE 1. Throughout the breeding period, a clinical score evaluation was given to both ears (six evaluation personnel performed scoring according to the evaluation standard in Table 5 and expressed a total score for both right and left ears).

TABLE 5

| Clinical Score | Signs |
| --- | --- |
| 1 | no simptoms |
| 2 | normal auricular shape, with scabs |
| 3 | hemorrhage from auricule, slight change of auricular shape |
| 4 | rhagades in auricule, conspicuous excoriation |
| 5 | conspicuous rhagades in auricule |

Figure 5:
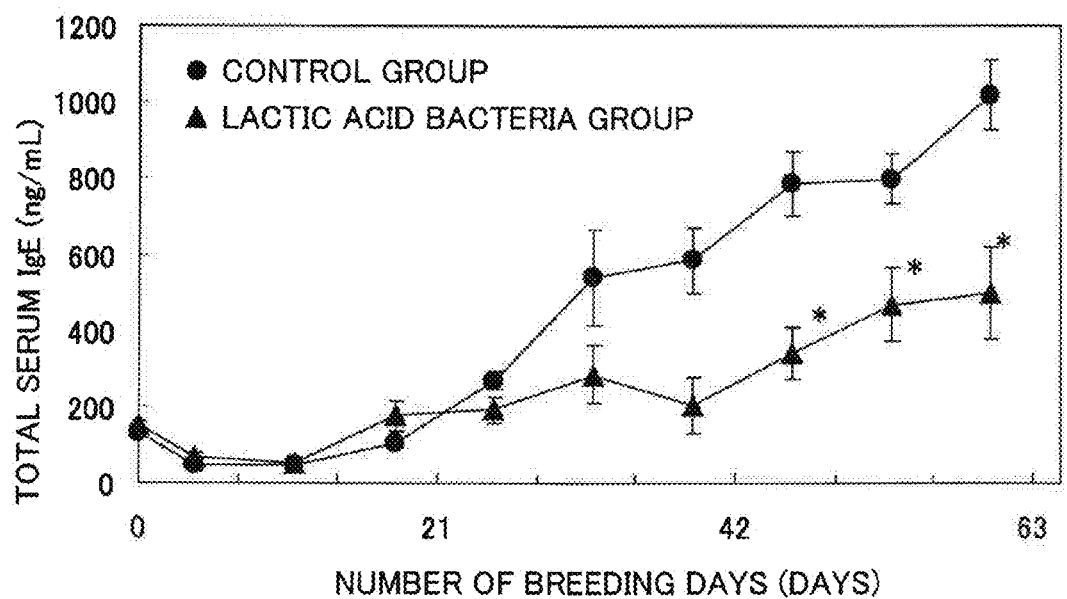
FIG. 5 is a graph showing the effect of repetitive oral administration of lactic acid bacteria on total serum IgE in an atopic dermatitis model animal.
Figure 6:
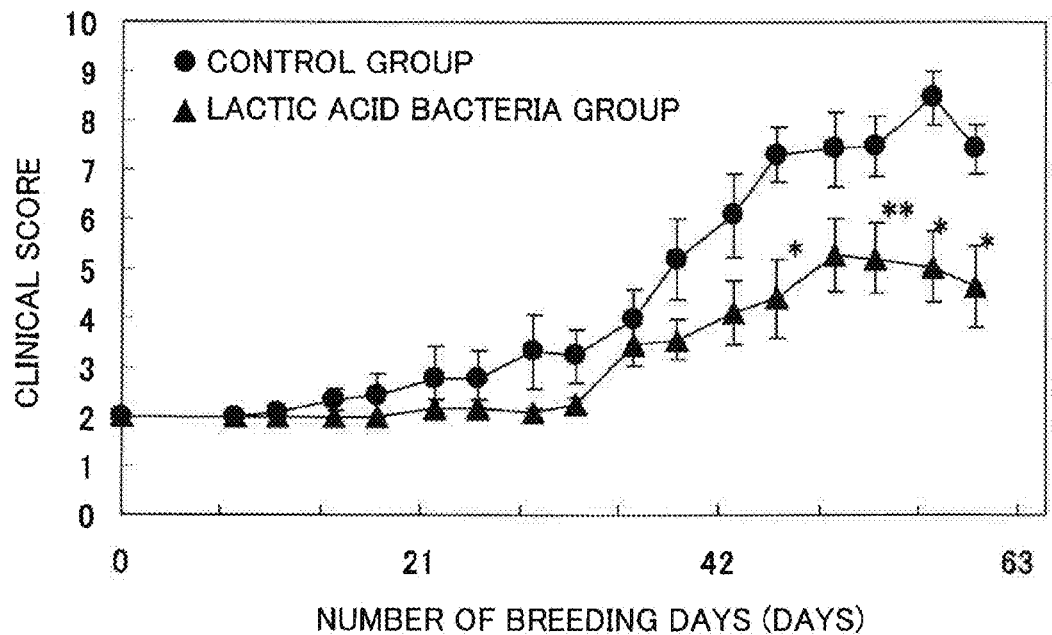
FIG. 6 is a graph showing the effect of repetitive oral administration of lactic acid bacteria on auricular allergic symptoms in an atopic dermatitis model animal.

The average dose of lactic acid bacteria in the lactic acid bacteria administration group was calculated from the feed ingestion amount and estimated to be 23 mg/mouse/day. The effect of repetitive oral administration of the lactic acid bacteria on total serum IgE in the model animal for atopic dermatitis is shown in FIG. 5 and the effect of repetitive oral administration of the lactic acid bacteria on auricular allergic symptoms in an atopic dermatitis model animal is shown in FIG. 6. In FIG. 5 and FIG. 6, the symbol * shows P<0.05 and the symbol ** shows P<0.01. In the lactic acid bacteria administration group, both IgE amount (FIG. 5) and clinical score (FIG. 6) were significantly reduced in comparison to the control group, and confirms that administration of lactic acid bacteria clearly reduces symptoms of atopic dermatitis. The results of the Student's t-test show that both total serum IgE and the clinical score of the lactic acid bacteria administration group were significantly reduced in comparison to the control group, and therefore confirm that administration of lactic acid bacterium according to the present invention clearly reduces symptoms of atopic dermatitis.

Example 5

3. Sensory Evaluation of Cooked Rice

Three go (about 450 g) of polished white rice (Koshihikari rice from Niigata Prefecture) were washed and immersed in 900 mL of distilled water. Nine mL of overnight culture liquid cultivated at 37° C. in MRS broth was added and gently mixed, and maintained at a temperature of 38° C. for one day. Thereafter the water was discarded, and after washing three times using approximately 500 mL of distilled water, a suitable amount of distilled water was added and the mixture was placed in an electrical rice cooker. A small amount of the rice before cooking was collected to measure the number of lactic acid bacteria using the same operation as EXAMPLE 1. As a result, $4.3 \times 10^8$ lactic acid bacteria were detected per 1 g of rice (dry weight conversion). Cooking was performed under normal conditions, and sensory evaluation of the cooked rice shows that it was delicious rice in no way inferior to normal cooked rice.

The invention claimed is:

1. An isolated lactic acid bacterium *Lactobacillus paracasei* K71 strain internationally deposited in the National Institute of Advanced Industrial Science and Technology, International Patent Organism Depositary under Accession No. FERM BP-11098.

2. An anti-allergic agent comprising the bacterium according to claim 1.

3. The agent according to claim 2, wherein the bacterium is a live bacterium.

4. The agent according to claim 2, wherein the bacterium is a killed bacterium.

5. A food composition including the agent according to claim 2.

6. A pharmaceutical composition including the agent according to claim 2.

7. A food composition including fermented rice using the bacterium according to claim 1, a pulverized product of the rice, or cooked rice obtained by cooking the above rice or the pulverized rice product.

8. A method of manufacturing an anti-allergic agent comprising the steps of inoculating a medium with the bacterium according to claim 1, and cultivating.

9. The method according to claim 8, wherein the medium is rice or a pulverized rice product.

10. A food composition including the agent according to claim 3.

11. A food composition including the agent according to claim 4.

12. A pharmaceutical composition including the agent according to claim 3.

13. A pharmaceutical composition including the agent according to claim 4.

* * * * *

SEQUENCE LISTING

<160> NUMBER OF SEQ ID NOS: 1

<210> SEQ ID NO 1
<211> LENGTH: 1530
<212> TYPE: DNA

```
<213> ORGANISM: Lactobacillus paracasei

<400> SEQUENCE: 1
gagtttgatc ctggctcagg atgaacgctg gcggcgtgcc taatacatgc aagtcgaacg      60
agttctcgtt gatgatcggt gcttgcaccg agattcaaca tggaacgagt ggcggacggg     120
tgagtaacac gtgggtaacc tgcccttaag tgggggataa catttggaaa cagatgctaa     180
taccgcatag atccaagaac cgcatggttc ttggctgaaa gatggcgtaa gctatcgctt     240
ttggatggac ccgcggcgta ttagctagtt ggtgaggtaa tggctcacca aggcgatgat     300
acgtagccga actgagaggt tgatcggcca cattgggact gagacacggc ccaaactcct     360
acgggaggca gcagtaggga atcttccaca atggacgcaa gtctgatgga gcaacgccgc     420
gtgagtgaag aaggctttcg ggtcgtaaaa ctctgttgtt ggagaagaat ggtcggcaga     480
gtaactgttg tcggcgtgac ggtatccaac cagaaagcca cggctaacta cgtgccagca     540
gccgcggtaa tacgtaggtg gcaagcgtta tccggattta ttgggcgtaa agcgagcgca     600
ggcggttttt taagtctgat gtgaaagccc tcggcttaac cgaggaagcg catcggaaac     660
tgggaaactt gagtgcagaa gaggacagtg gaactccatg tgtagcggtg aaatgcgtag     720
atatatggaa gaacaccagt ggcgaaggcg gctgtctggt ctgtaactga cgctgaggct     780
cgaaagcatg ggtagcgaac aggattagat accctggtag tccatgccgt aaacgatgaa     840
tgctaggtgt tggagggttt ccgcccttca gtgccgcagc taacgcatta agcattccgc     900
ctggggagta cgaccgcaag gttgaaactc aaaggaattg acggggcccc gcacaagcgg     960
tggagcatgt ggtttaattc gaagcaacgc gaagaacctt accaggtctt gacatctttt    1020
gatcacctga gagatcaggt ttccccttcg ggggcaaaat gacaggtggt gcatggttgt    1080
cgtcagctcg tgtcgtgaga tgttgggtta agtcccgcaa cgagcgcaac ccttatgact    1140
agttgccagc atttagttgg gcactctagt aagactgccg gtgacaaacc ggaggaaggt    1200
ggggatgacg tcaaatcatc atgccccttta tgacctgggc tacacacgtg ctacaatgga    1260
tggtacaacg agttgcgaga ccgcgaggtc aagctaatct cttaaagcca ttctcagttc    1320
ggactgtagg ctgcaactcg cctacacgaa gtcggaatcg ctagtaatcg cggatcagca    1380
cgccgcggtg aatacgttcc cgggccttgt acacaccgcc cgtcacacca tgagagtttg    1440
taacacccga agccggtggc gtaacccttt tagggagcga gccgtctaag gtgggacaaa    1500
tgattagggt gaagtcgtaa caaggtagcc                                      1530
```